US012446867B1

(12) United States Patent
Turner et al.

(10) Patent No.: US 12,446,867 B1
(45) Date of Patent: Oct. 21, 2025

(54) SPECIMEN RETRIEVAL APPARATUS AND METHODS

(71) Applicant: Kobex LLC, Cheyenne, WY (US)

(72) Inventors: Aaron Turner, Cheyenne, WY (US); Connie Hong, Cheyenne, WY (US); John H. Shadduck, Cheyenne, WY (US)

(73) Assignee: Kobex LLC, Cheyenne, WY (US)

( * ) Notice: Subject to any disclaimer, the term of this patent is extended or adjusted under 35 U.S.C. 154(b) by 0 days.

(21) Appl. No.: 18/891,231

(22) Filed: Sep. 20, 2024

(51) Int. Cl.
*A61B 10/04* (2006.01)
*A61B 10/02* (2006.01)

(52) U.S. Cl.
CPC ...... *A61B 10/04* (2013.01); *A61B 2010/0208* (2013.01)

(58) Field of Classification Search
CPC .............. A61B 2017/00287; A61B 2010/0208
See application file for complete search history.

(56) References Cited

U.S. PATENT DOCUMENTS 5,853,374 A 12/1998 Hart et al.
8,430,826 B2 4/2013 Uznanski et al.
8,486,087 B2 7/2013 Fleming
8,585,712 B2 11/2013 O'Prey et al.
8,652,147 B2 2/2014 Hart
8,721,658 B2 5/2014 Kahle et al.
8,734,464 B2 5/2014 Grover et al.
8,777,961 B2 7/2014 Cabrera et al.
8,906,036 B2 12/2014 Farascioni
8,956,370 B2 2/2015 Taylor et al.
8,968,329 B2 3/2015 Cabrera
9,005,215 B2 4/2015 Grover et al.
9,017,340 B2 4/2015 Davis
9,033,995 B2 5/2015 Taylor et al.
9,084,588 B2 7/2015 Farascioni
9,113,849 B2 8/2015 Davis
9,247,947 B2 2/2016 Uznanski et al.
9,370,378 B2 6/2016 O'Prey et al.
9,549,747 B2 1/2017 Carlson
9,579,115 B2 2/2017 Kahle et al.
9,622,730 B2 4/2017 Farascioni
9,949,748 B2 4/2018 Taylor et al.
9,993,229 B2 6/2018 Whitfield
10,219,830 B2 3/2019 Wachli et al.
10,219,831 B2 3/2019 Wachli et al.
10,245,053 B2 4/2019 Taylor et al.
10,258,317 B2 4/2019 Carlson
10,327,745 B2 6/2019 Cabrera
10,463,352 B2 11/2019 Do et al.
10,537,345 B2 1/2020 Kahle et al.
10,568,659 B2 2/2020 Do et al.
(Continued)

FOREIGN PATENT DOCUMENTS

CN 213283109 U * 5/2021

*Primary Examiner* — Martin T Ton
(74) *Attorney, Agent, or Firm* — Levine Bagade Han LLP

(57) ABSTRACT

A laparoscopic tissue retrieval bag for minimally invasive surgery and comprising a high-strength, biocompatible film wall that is transparent or translucent. The retrieval bag wall is collapsible and crushable for ease of insertion through a laparoscopic cannula. The retrieval bag further comprises a plurality of lifting band or elements in the retrieval bag wall and extending from the open proximal end towards the closed distal end.

15 Claims, 19 Drawing Sheets

(56) References Cited

U.S. PATENT DOCUMENTS

| | | | |
|---|---|---|---|
| 10,653,400 B2 | 5/2020 | Kamaraj et al. | |
| 10,667,800 B2 | 6/2020 | Prior | |
| 10,792,023 B2 | 10/2020 | Prior | |
| 10,792,057 B2 | 10/2020 | Prior et al. | |
| 10,842,530 B2 | 11/2020 | Wachli et al. | |
| 10,987,132 B2 | 4/2021 | Wachli et al. | |
| 11,045,176 B2 | 6/2021 | George et al. | |
| 11,051,795 B2 | 7/2021 | Baril et al. | |
| 11,051,834 B2 | 7/2021 | Baril et al. | |
| 11,065,051 B2 | 7/2021 | Prior | |
| 11,071,559 B2 | 7/2021 | Baril et al. | |
| 11,083,443 B2 | 8/2021 | Prior | |
| 11,083,490 B2 | 8/2021 | Prior et al. | |
| 11,134,931 B2 | 10/2021 | Prior | |
| 11,134,932 B2 | 10/2021 | Banerjee et al. | |
| 11,160,543 B2 | 11/2021 | Baril et al. | |
| 11,172,915 B2 | 11/2021 | Baril et al. | |
| 11,172,949 B2 | 11/2021 | Baril et al. | |
| 11,191,557 B2 | 12/2021 | Taylor et al. | |
| 11,191,559 B2 | 12/2021 | George et al. | |
| 11,224,413 B2 | 1/2022 | Baril et al. | |
| 11,253,240 B2 | 2/2022 | Baril et al. | |
| 11,304,687 B2 | 4/2022 | Baril et al. | |
| 11,304,714 B2 | 4/2022 | Baril et al. | |
| 11,344,284 B2 | 5/2022 | Baril et al. | |
| 11,357,524 B2 | 6/2022 | Kahle et al. | |
| 11,369,352 B2 | 6/2022 | Baril et al. | |
| 11,406,369 B2 | 8/2022 | Baril et al. | |
| 11,426,151 B2 | 8/2022 | Baril et al. | |
| 11,446,015 B2 | 9/2022 | George et al. | |
| 11,517,297 B2 | 12/2022 | Baril et al. | |
| 11,547,428 B2 | 1/2023 | Taylor et al. | |
| 11,547,444 B2 | 1/2023 | Wachli et al. | |
| 11,666,351 B2 | 6/2023 | Prior et al. | |
| 11,707,263 B2 | 7/2023 | Taylor et al. | |
| 11,707,264 B2 | 7/2023 | Mickus et al. | |
| 11,737,782 B2 | 8/2023 | Wachli et al. | |
| 11,744,612 B2 | 9/2023 | Do et al. | |
| 11,759,188 B2 | 9/2023 | Matta et al. | |
| 11,805,999 B2 | 11/2023 | Banerjee et al. | |
| 11,857,216 B2 | 1/2024 | Prior et al. | |
| 11,871,917 B2 | 1/2024 | Kessler et al. | |
| 11,918,197 B2 | 3/2024 | Do et al. | |
| 2005/0267492 A1* | 12/2005 | Poncet | A61B 17/221 606/114 |
| 2007/0088370 A1* | 4/2007 | Kahle | A61B 17/221 606/114 |
| 2011/0184432 A1* | 7/2011 | Parihar | A61B 17/00234 606/114 |
| 2011/0184436 A1* | 7/2011 | Shelton, IV | A61B 17/00234 606/114 |
| 2019/0328377 A1* | 10/2019 | Johnson | A61B 17/32056 |
| 2020/0085455 A1* | 3/2020 | George | A61B 17/3423 |
| 2021/0236104 A1* | 8/2021 | Matta | A61B 17/00234 |

* cited by examiner

SPECIMEN RETRIEVAL APPARATUS AND METHODS

FIELD OF THE INVENTION

This disclosure relates generally to the field of laparoscopic tissue retrieval bags and, more specifically, to a retrieval bag with lifting bands that allow the clinician to elevate the bottom end of the retrieval bag upwardly to position a tissue specimen closer to a minimally invasive incision in the patient's body wall to allow for cutting of the tissue specimen for retraction through the incision.

SUMMARY OF THE INVENTION

The present disclosure includes a tissue retrieval system including a tissue retrieval bag. In one variation, such a tissue retrieval system includes a retrieval bag having an open end and a bag wall around an interior space extending to a closed end, the retrieval bag having a rim portion at the open end; the retrieval bag adapted for an extended position wherein the closed end is extended a selected depth away from the rim portion and progressively collapsed positions wherein the closed end is lifted toward the open end; and a plurality of lifting members carried in the bag wall configured for lifting the closed end toward the open end.

The bags described herein can have a bag wall that is assembled from a polymeric thin film material.

Additional variations of the tissue retrieval system include a retrieval bag where the plurality of lifting members include at least one of a polymeric thin film material and a thread. However, the materials can comprise any material commonly used in such applications. Alternatively, the plurality of lifting members can comprise different materials. In some variations, one or more of the plurality of lifting members are at least partly elastic. In additional variations, least one of the plurality of lifting members has a width of 40 mm or less. One or more of the lifting members can have a width ranging from 0.5 mm to 40 mm.

The plurality of lifting members can be carried in guide channels. In some variations, the bag wall is configured with at least three guide channels each with a lifting member therein. The adjacent guide channels in the bag wall can optionally at least partly overlap.

Variations of the tissue retrieval system can include a width of a guide channel in the bag wall is greater than the width of a lifting member from the plurality of lifting members disposed therein.

In some variations, the tissue retrieval system can include a support ring coupled to a rim portion of the retrieval bag around the open end of the retrieval bag. The support ring can be attachable and detachable from the rim portion. In additional variations, the support ring is fixed in the rim portion.

Additional variations of the tissue retrieval system can further include an introducer sleeve extending about a longitudinal axis to a distal tip; wherein the retrieval bag is foldable for a pre-deployed configuration for carrying in an interior passageway of the introducer sleeve; and an elongate deployment member axially translatable in the interior passageway to extend to retrieval bag outward from the distal tip of the introducer sleeve.

The tissue retrieval system can also have an elongate deployment member that is coupled to at least one spring element adapted to hold open the open end of the retrieval bag.

The present disclosure also includes methods of retrieval of a retrieval bag. For example, such a method can include providing a retrieval bag having an open end and a bag wall extending to a closed end; positioning the retrieval bag in a body cavity of a patient; disposing a tissue specimen in the retrieval bag; withdrawing the open end of the retrieval bag through an access incision accessing the body cavity; and lifting a plurality of lifting members carried in a wall of the retrieval bag to thereby lift the closed end of the retrieval bag and the tissue specimen into the access incision to facilitate cutting the tissue specimen.

Variations of method can include the plurality of lifting members being at least partly elastic to thereby apply a continuous lifting force on the closed end of the retrieval bag and the tissue specimen.

13 illustrates another variation of a retrieval system with an occluder member carried on the introducer sleeve in the form of a balloon.

Figure 14A:
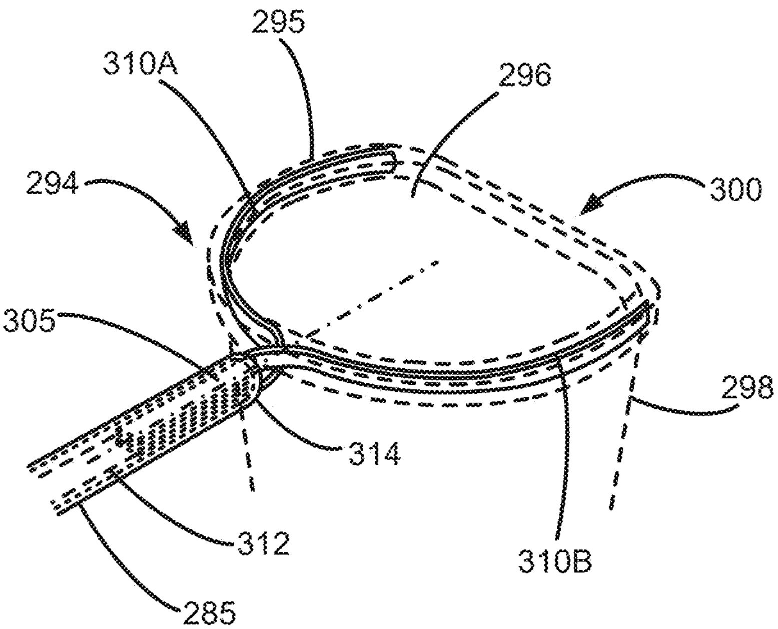

FIG. 14A illustrates another variation of a retrieval system with an extendable deployment member having a living hinge portion proximal to the spring arms for tilting the bag rim.

Figure 14B:
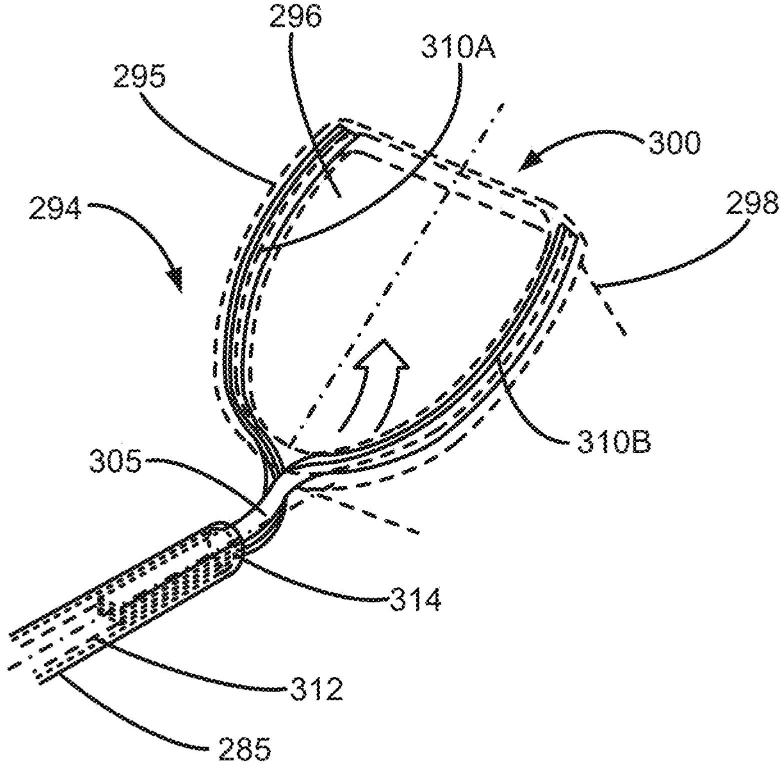

FIG. 14B illustrates the living hinge and spring arms extended outwardly from the introducer sleeve which then tilts the bag rim.

Figure 15A:
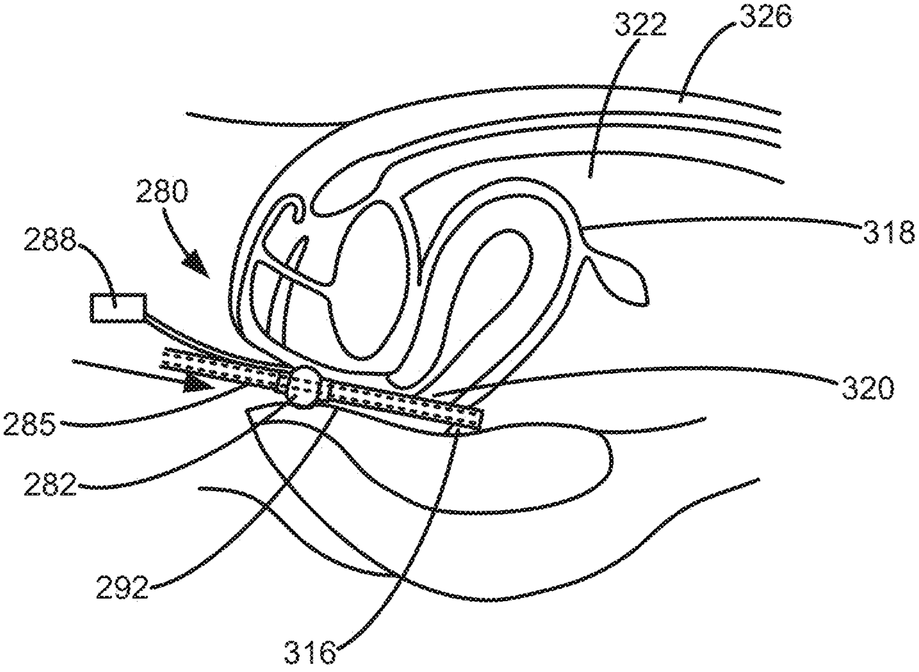

FIG. 15A schematically illustrates using the retrieval system of FIGS. 12, 14A, and 14B in a trans-vaginal access with the occluder disposed in the vaginal canal of the patient.

Figure 15B:
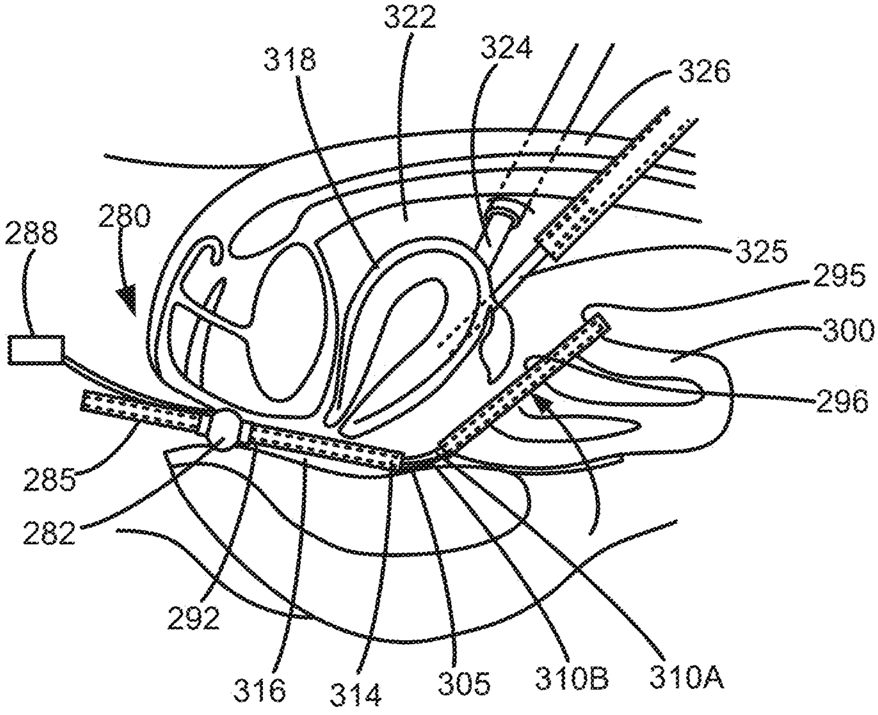

FIG. 15B illustrates a subsequent step of the method with the retrieval bag deployed and the living hinge tilting the bag rim.

Figure 15C:
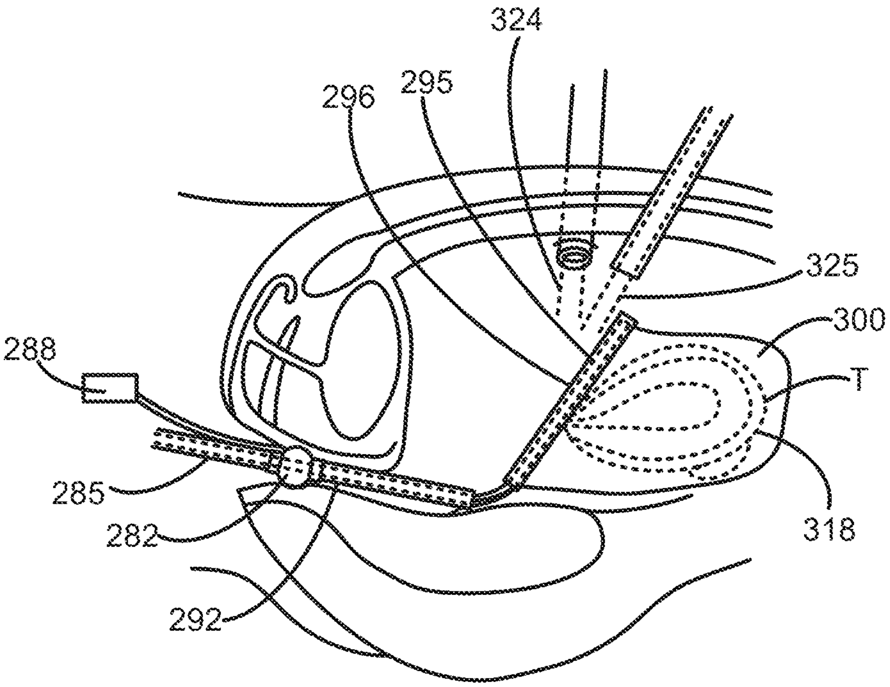

FIG. 15C illustrates a subsequent step wherein the clinician has mobilized the uterus and inserted the tissue specimen into the retrieval bag with graspers.

Figure 7A:
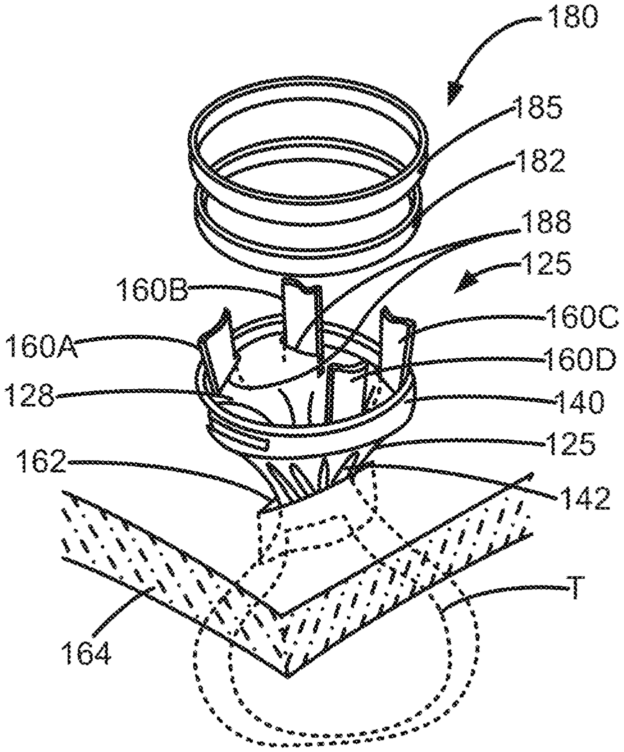
FIG. 7A is a view of the retrieval bag of the type shown in FIGS. 4-5 4 after the bag rim has been withdrawn through an incision in a body wall with a support ring assembly above the bag.
Figure 7B:
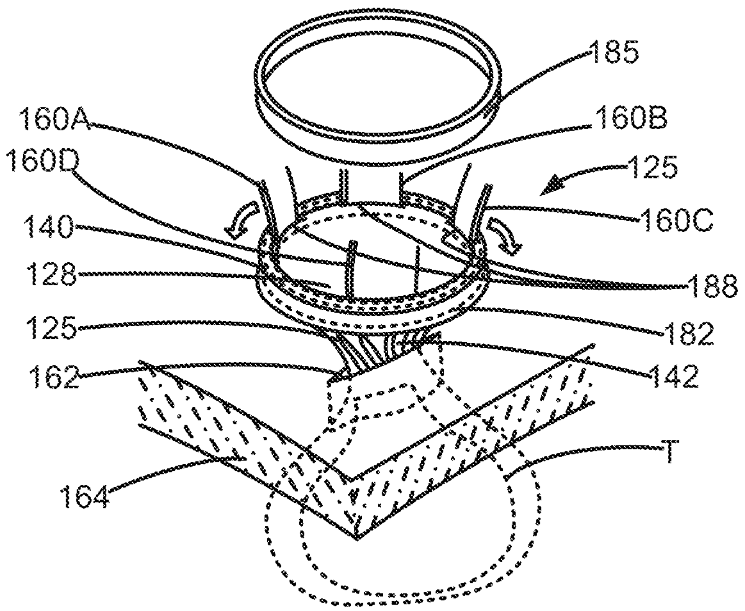
FIG. 7B shows the rim of the bag folded over an inner support ring.
Figure 7C:
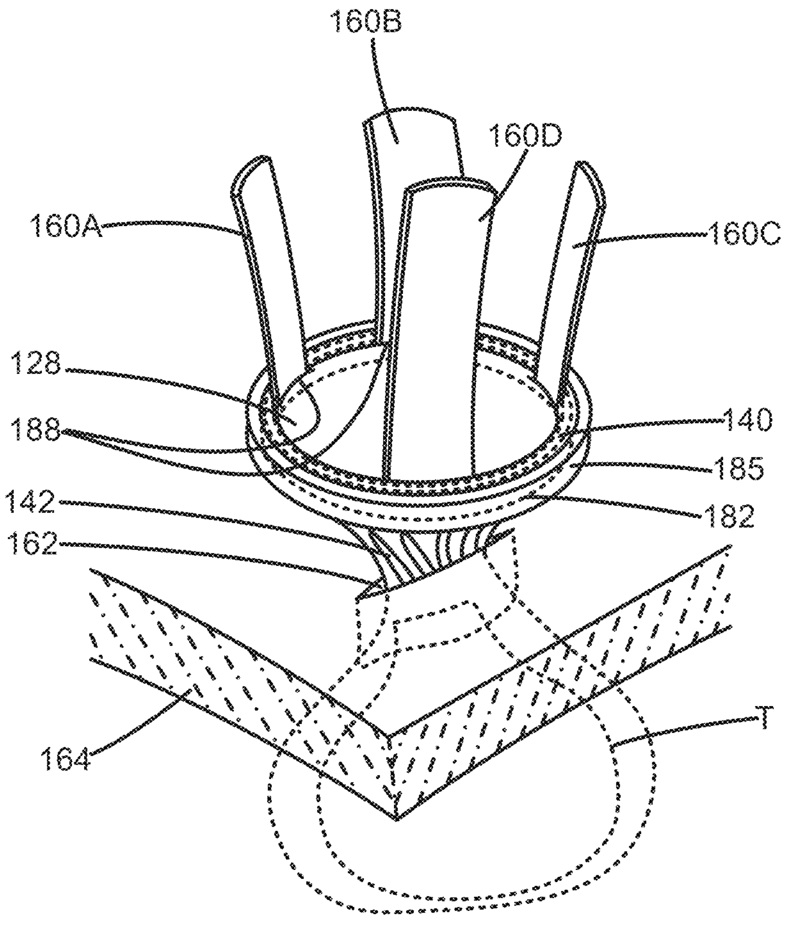
FIG. 7C shows the outer support ring pressed downwardly over the inner support ring to capture the bag rim in a substantially rigid open configuration.
Figure 15D:
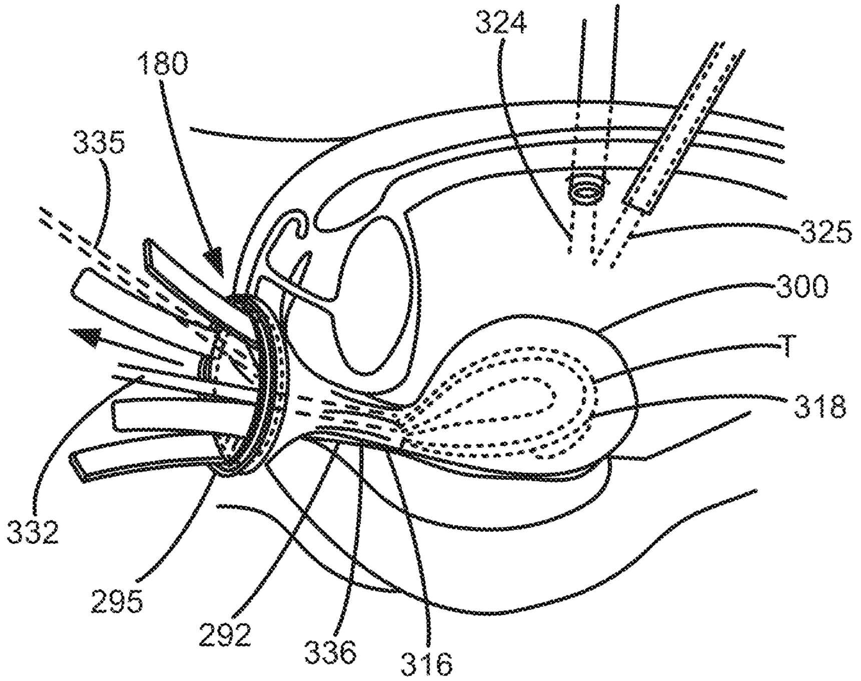

FIG. 15D illustrates a subsequent step wherein the retrieval bag rim is withdrawn through the incision, and the support ring assembly are coupled to the bag rim as shown in FIGS. 7A-7C.

15E illustrates a subsequent step wherein the lifting bands are lifted, the bag rim and support rings are pressed against the exterior of the body wall, and the tissue specimen and bag wall are pulled into the incision, which retracts outwardly the walls of the incision.

Figure 16:
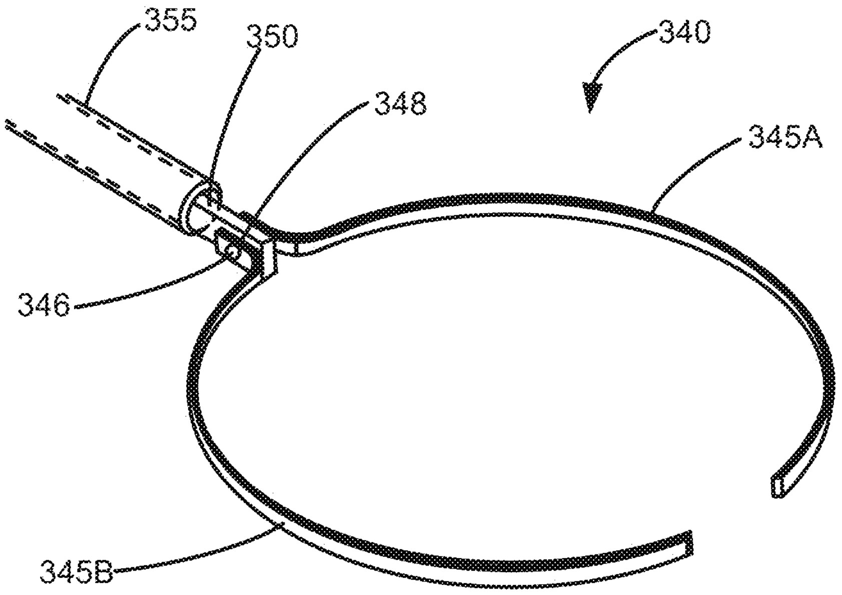

FIG. 16 illustrates another variation of a retrieval system wherein the spring arms are coupled to a pivot pin to allow tilting of the retrieval bag rim.

Figure 17:
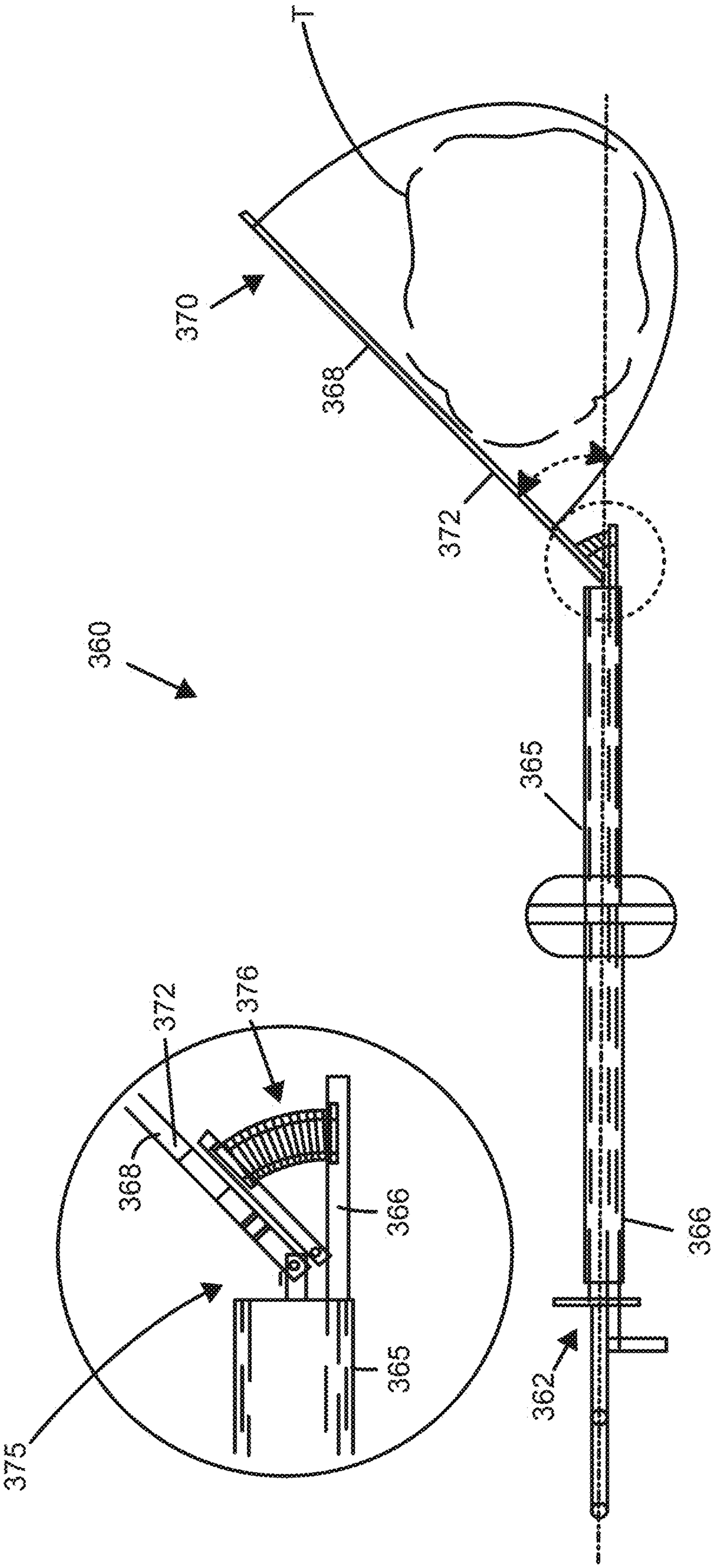

FIG. 17 illustrates another variation of a retrieval system with a tilting bag rim that uses an extendable actuator member in the introducer sleeve to actuate tilting of the bag rim.

DETAILED DESCRIPTION

Figure 1:
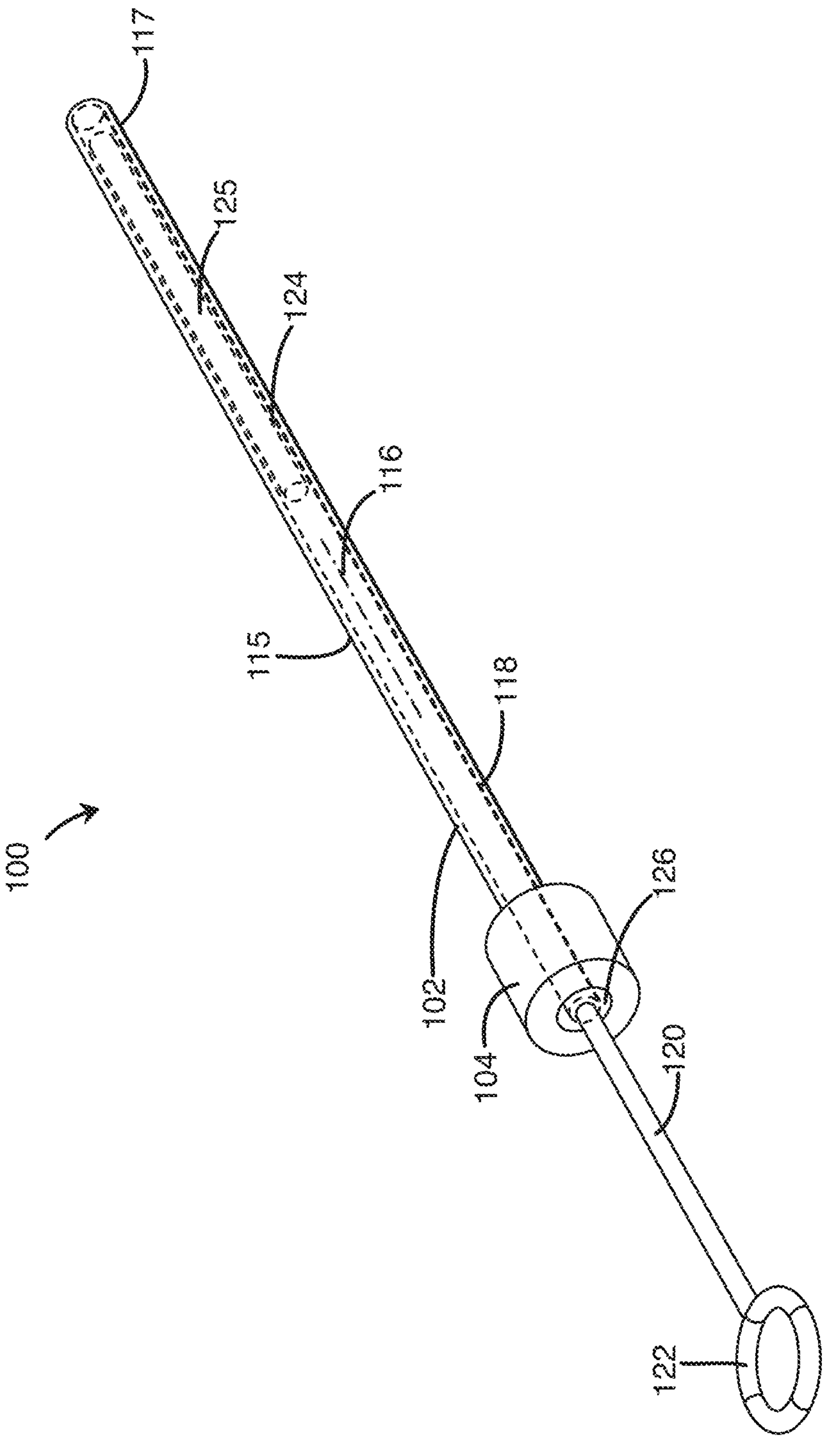
FIG. 1 is a perspective view of a tissue retrieval system with a retrieval bag in a non-deployed position in an introducer sleeve.
Figure 2:
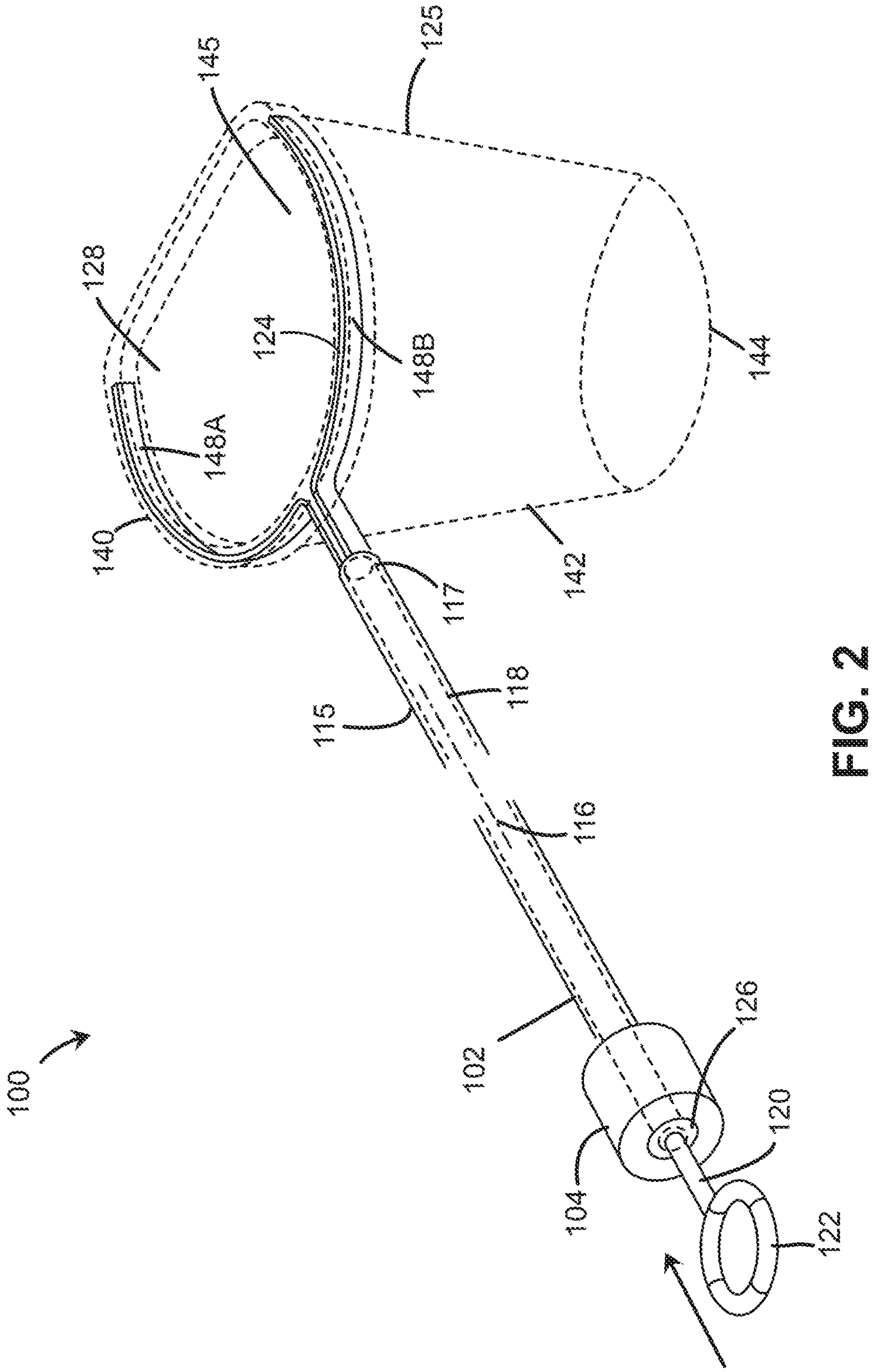
FIG. 2 is a perspective view of the system of FIG. 1 with the retrieval bag in a deployed position in phantom view wherein springs arms open the rim of the bag.

Referring to FIGS. 1 and 2, the tissue retrieval system 100 corresponding to the invention is shown which includes an introducer device 102 having a proximal handle 104 coupled to an elongated introducer sleeve 115 extending about longitudinal axis 116 to a distal end 117. The handle 104 and introducer sleeve 115 have an axial-extending interior passageway 118 therein that receives an axially-slidable deployment shaft 120 with a proximal grip 122 and a distal portion 124 that carries a retrieval bag 125 (FIG. 2). The retrieval bag 125 is adapted for folding into a collapsed, pre-deployed configuration that is retractable into the interior passageway 118 of the introducer sleeve 115 as shown in FIG. 1.

In FIG. 2, it can be seen that the deployment shaft 120 is moved distally by a clinician to an extended position wherein the retrieval bag 125 is extended outwardly from the distal end 117 of the introducer sleeve 115. In the extended position of FIG. 2, the retrieval bag 125 (in phantom view) unfolds into a deployed configuration within a patient's body, such as in an abdominal cavity. The handle 104 carries a seal 126 around the deployment shaft 120 in interior passageway 118 to prevent loss of an insufflation gas from the body cavity. The clinician can rotate or axially translate the deployment shaft 120 to orient the retrieval bag 125 to a position suitable for receiving a tissue specimen that is grasped by a separate grasping instrument as will be further described below. In other variations shown below, the retrieval bag 125 can also be tilted or angled by a mechanism in the deployment shaft 120 or introducer sleeve 115.

In a variation shown in FIGS. 2 and 3, the retrieval bag 125 has an open end 128 with a rim portion 140 and a bag wall 142 that extends to a closed bottom end 144. bag wall 142 comprises an arrangement of thin film materials described further below that extend from the rim portion 140 to the closed end 144 defining an interior space 145 in the bag for holding a retrieved tissue specimen. The bag 125 typically has a wall 142 that tapers to toward the closed bottom end 144 but the bag wall 142 also can have no taper or can taper to an apex at the bag bottom end. The diameter of the open end 128 of the bag 125 can range from 40 mm to 120 mm with a bag volume ranging from 1,000 cc to 7,000 cc.

Figure 3:
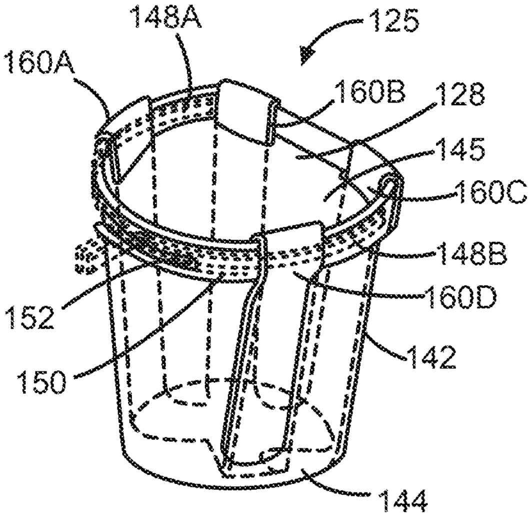
FIG. 3 is a perspective view of the retrieval bag of FIG. 2 in a deployed position with the spring arms in phantom view and lifting bands folded against the bag wall.

In a variation shown in FIGS. 2 and 3, deployment shaft 120 has a distal portion 124 that is detachable from the rim portion 140 of the retrieval bag 125 and comprises spring arms 148A and 148B for holding open the open end 128 of the retrieval bag 125 during a step of a method of using the retrieval bag 125. In FIG. 3, it can be seen that the spring arms 148A 148B (in phantom view) are insertable and removable from a channel 150 in the thin-film wall 142 of the rim portion 140 of the retrieval bag (FIG. 3). Each spring arm 148A, 148B is inserted through opening 152 in the wall 142 of the rim portion 140 that accesses the channel 150. The spring arms 148A 148B are configured to collapse to a pre-deployed, tensioned position with the folded retrieval bag 125 when retracted into the passageway 118 of the introducer sleeve 115 as shown in FIG. 1.

Figure 4:
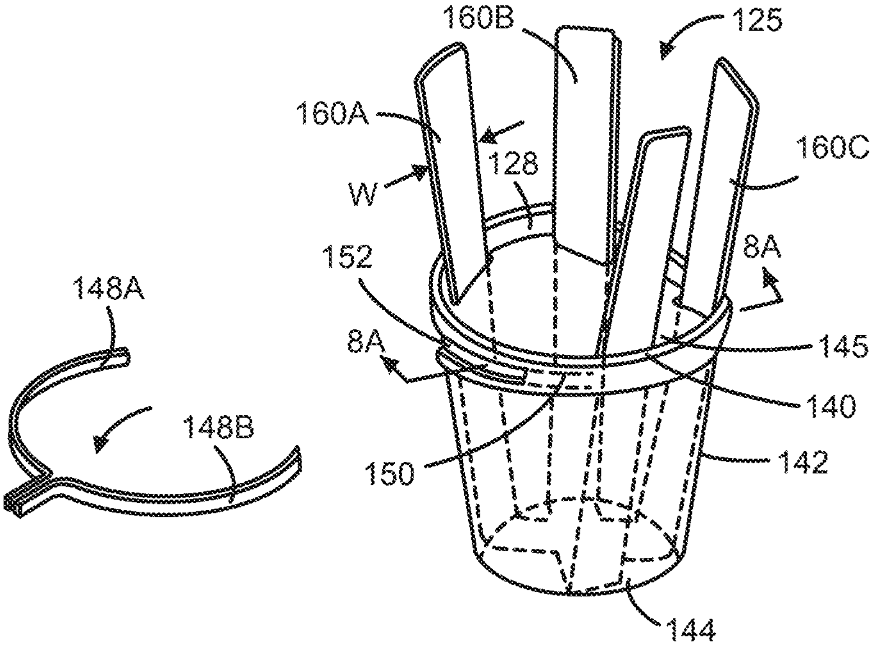
FIG. 4 is a schematic view of the retrieval bag of FIG. 3 with the spring arms withdrawn from the bag rim and the lifting bands in a lifting position.

The retrieval bag 125 in FIG. 3 has four lifting elements or bands 160A-160D shown in FIG. 3, folded over the bag wall 142 as when the bag is prepared for folding for insertion in the interior passageway 118 of the introducer sleeve 115. FIG. 4 illustrates the retrieval bag 125 separated from spring arms 148A, 148B and the introducer sleeve 115 to show the function of the various components of the bag 125. In the variation of FIGS. 3 and 4, the retrieval bag 125 is configured with four lifting elements or bands 160A-160D although from 2 to 20 lifting bands are possible. In FIG. 4, the lifting bands 160A-160D are unfolded and extended upwardly from the rim portion 140 of the bag 125 as when prepared to be lifted.

Figure 5:
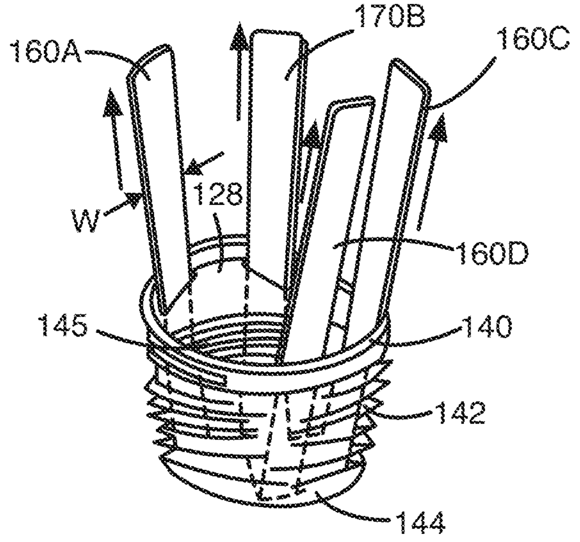
FIG. 5 is a schematic view of the retrieval bag of FIG. 4, showing the lifting bands actuated to lift the bottom of the bottom of the bag upwardly.

In a method of use further described below, a tissue specimen is captured in the interior space 145 of bag 125 within a patient's body cavity, and the rim portion 140 and open end 128 of the bag 125 are collapsed and withdrawn through a minimally invasive incision 162 that accesses the body cavity through a body wall 164 (see FIGS. 7A-7C). The function of the lifting bands 160A-160D is to allow the clinician to lift the bottom end 144 of the bag upwardly toward the rim portion 140 and open end 128 of the bag 125 that is outside the patient's body. The lifting bands 160A-160D thereby lift the tissue specimen in the bag 125 toward the minimally-invasive incision 162 in the body wall 164. With an uppermost portion of the tissue specimen then exposed in the incision 162, the clinician can then use a scalpel, other manual cutting device, or a motor-driven cutting device to cut the tissue specimen in a suitable manner to allow removal of the tissue through the minimally invasive incision 162 in the body wall. More in particular, FIG. 5 shows the bag 125 when the lifting bands 160A-160D are lifted to show the accordion-like collapse of the bag wall 142 and lifting of the bag bottom 144 towards the rim portion 140.

Figure 6A:
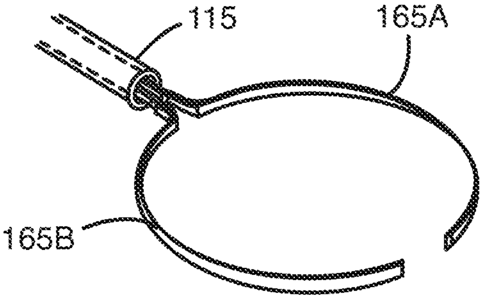
FIG. 6A is a perspective view of another variation of spring arms configured for holding open the bag rim.
Figure 6B:
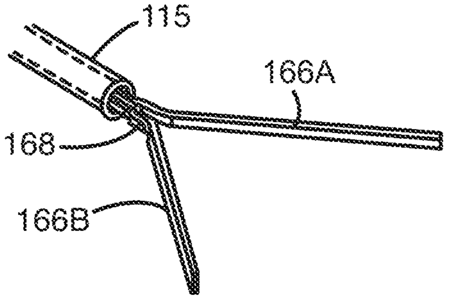
FIG. 6B is a view of another variation of spring arms.

The variation of tissue retrieval system 100 of FIG. 2 shows the spring arms 148A, 148B having a curved or part-circular shape that extends at least 180° around the perimeter of the rim portion 140, but other shapes are possible. FIG. 6A shows spring arms 165A 165B that again have a part-circular shape that extends closer to 360° around the perimeter of the rim portion of a bag compared to the variation of FIG. 2. FIG. 6B shows spring arms 166A, 166B that have a substantially straight shape extending distally from a living hinge portion 168.

As will be illustrated below in FIG. 7A-7C, the retrieval bag 125 has a wall 142 around the captured tissue specimen T that is specifically configured to prevent a scalpel or other cutting tool from cutting through the portion of the bag wall 142 that is withdrawn into a minimally invasive incision 162. In a method of use, the clinician cuts the tissue specimen T that is exposed in the incision 162 to reduce its size or cross-section, wherein the clinician must be careful not to cut through bag wall 142 in the incision 162. For this reason, the layers of the bag wall 142 are configured to be resistant to cutting. Further, the lifting bands 160A-160D have a selected width W (FIGS. 4-5) so that when the bag wall 142 is circumferentially compressed in the incision 162 as shown in FIG. 7A, the lifting bands 160A-160D overlap one another to provide additional layers of thin-film material that increases resistance to cutting through the several layers of film in the bag wall 142.

Figure 8A:
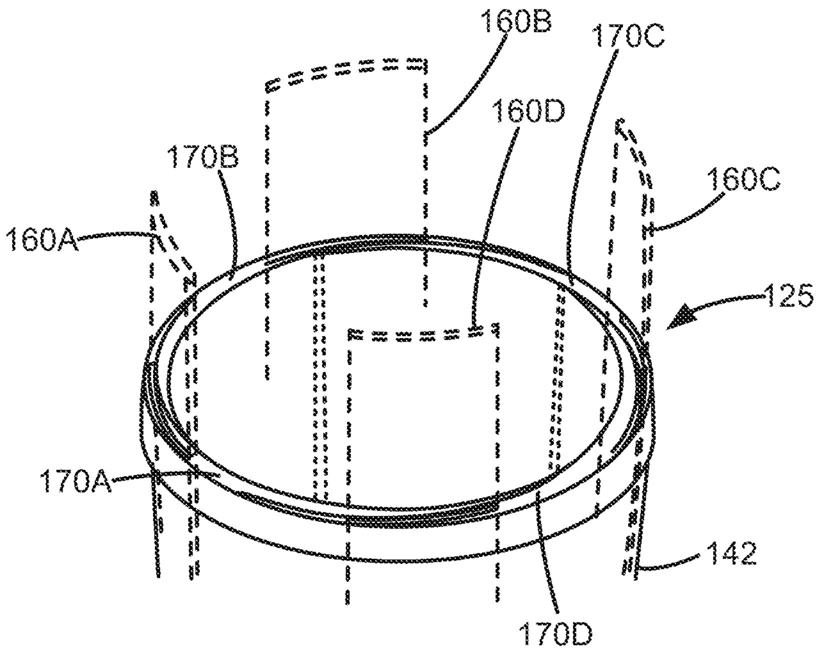
FIG. 8A is a sectional view of the retrieval bag of FIGS. 4 and 7A-7C, showing that the lifting bands are carried in overlapping guide channels in the bag wall.
Figure 8B:
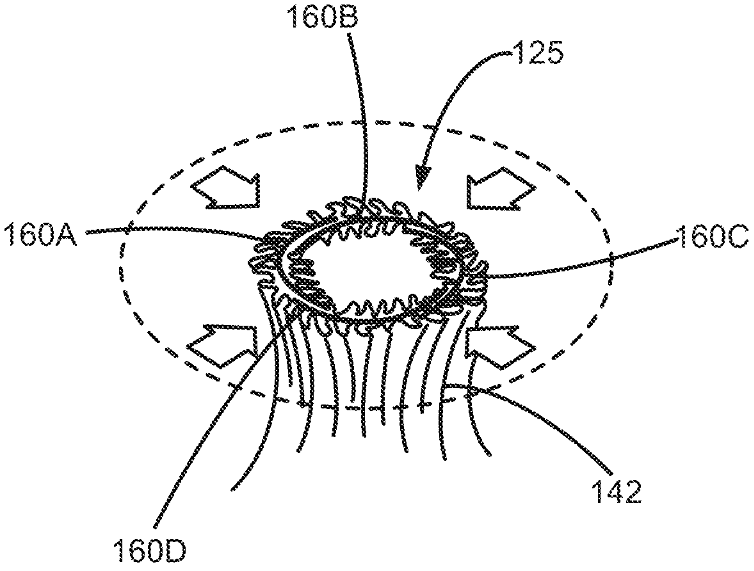
FIG. 8B shows the bag wall of FIG. 8A compressed as in an incision wherein the lifting bands overlap in the guide channels.

Now turning to FIGS. 8A and 8B, the sectional views of wall 142 of bag 125 illustrate that the lifting bands 160A-160D are carried in guide channels 170A-170B formed between thin-film layers of the wall 142 wherein each channel 170A-170B overlaps an adjacent channel. In the schematic sectional view of FIG. 8B, it can be seen that the lifting bands 160A-160D will overlap when the bag wall 142 is circumferentially compressed as when collapsed and compressed within an incision 162 (see FIG. 7A) which may have an incision length of 10 mm to 30 mm.

Referring to FIGS. 8A and 8B, the bag wall 142 comprises multiple layers of a high-strength, thin-film polymeric material that is foldable to a compact form for positioning in passageway 118 of the introducer sleeve 115 (FIG. 1). Further, the bag wall 142 is collapsible when circumferentially compressed in an incision 162 (FIG. 8B). Examples of suitable materials for the bag wall 142 and lifting bands 160A-160D include biocompatible polymers such as polyethylene terephthalate (PET), polyimide (Kapton), polypropylene, or a combination thereof. The thin-film material can also be combined with cut-resistant thread elements or woven elements such as Kevlar to provide additional resistance to cutting. The lifting bands can be made of a similar material. The thin-film materials are typically transparent or translucent to observe the tissue specimen captured in the bag 125. As described further below, the lifting bands 160A-160D can also be at least partly an elastomeric material to apply a continuous lifting force on the bag wall. In a variation, the lifting bands 160A-160D have a width W of 40 mm or less, and often range between 10 mm and 25 mm in width. The scope of the invention includes lifting bands or members 160A-160D that comprise a plurality of cords, threads or bands for lifting the bag wall that has a small diameter or width, for example, 0.5 mm or greater.

Now, referring to FIGS. 7A and 7B, in a variation, an additional component of the retrieval bag 125 comprises a support ring assembly 180 that is adapted to hold open the open end 128 of the bag 125 after the bag rim portion 140 is withdrawn through the minimally invasive incision 162 in the patient's body wall 164. In a variation, the support ring assembly 180 comprises an inner ring 182 and an outer ring 185 that have cooperating nesting diameters and are adapted to lock the rim portion 140 of the bag 125 between the inner and outer rings. The inner and outer rings 182, 185 typically are molded of a flexible resilient plastic. FIG. 7A shows the open end 128 and rim portion 140 of the bag 125 pulled upward through the incision 162 with inner and outer rings 182, 185 prepared for use. FIG. 7B shows the rim portion 140 of the bag pulled upward through the inner ring 182 with the rim portion 140 then folded outwardly and downward over inner ring 182. FIG. 7C then illustrates the outer ring 185 inserted over the inner ring 182 and bag wall 142 to lock the ring assembly 180 together with the bag rim 140 sandwiched between the rings 182 185.

In FIG. 7A-7C, it can be seen that the lifting bands 160A-160B extend outwardly from guide channel openings 188 that are recessed downwardly from the rim portion 140. This arrangement of the openings 188 thus allows the rim portion 140 of bag 125 to be folded over the inner ring 182, as shown in FIG. 7B and locked in place between the rings so that the guide channel openings 188 are positioned around the superior edge of the support ring assembly 180 and bag 125. In this configuration, the lifting bands 160A-160D can then be lifted directly upward to elevate the tissue specimen T into the incision 162.

Figure 9A:
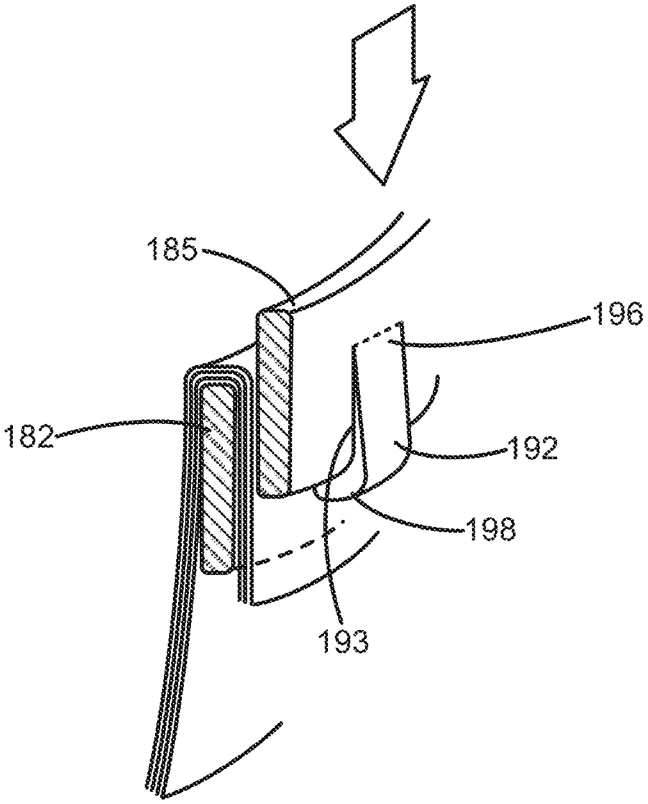
FIG. 9A shows a snap-lock latch element between the inner and outer support rings of FIG. 7A-7C.
Figure 9B:
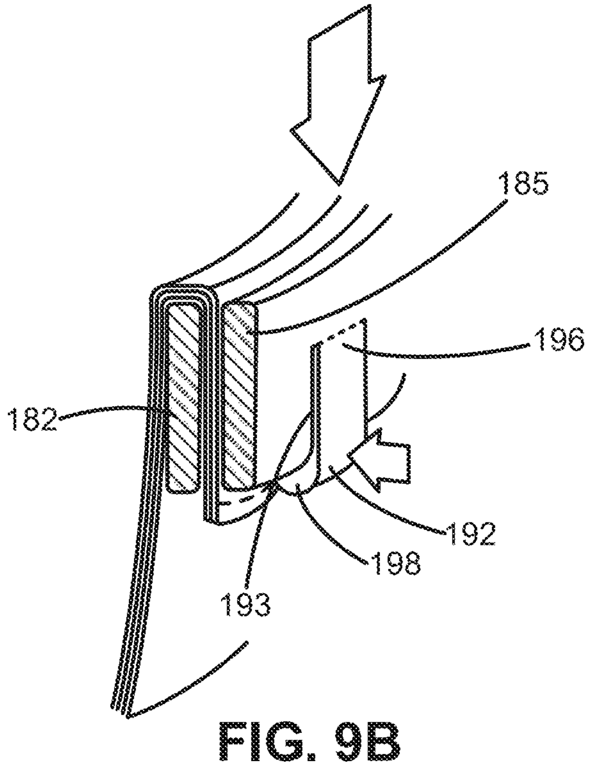
FIG. 9B shows the snap-lock latch element of FIG. 9A in a locked position.

As can be seen in FIGS. 7A-7C, the inner and outer rings 182, 185 are dimensioned to nest together in a slip fit over bag wall 142 to maintain the open end 128 of bag 125 in its supported open shape. FIGS. 9A and 9B show a cut-away partial view of another variation. The outer ring 185 has a plurality of flex-lock features for locking the two rings in registration with one another. For example, FIG. 9A illustrates one of a plurality of flex-latch elements 192 on the outer ring 185. Each latch element 192 has partial slots 193 in the wall 194 of the ring 185, which allows the latch element to flex outward about living hinge portion 196 as the outer ring 185 is pressed over the inner ring 182 and bag wall 142. FIG. 9B shows a projecting bottom edge 198 of the flex-latch element 192 snapping inward under the inner ring 182. In another variation, the upper edge of the outer ring 185 can be configured with inwardly projecting tabs (not shown) for aligning the top edges of the inner and outer rings 182 185. Various cooperating snap-latch features known in the art can be provided on either or both of the inner and outer rings 182, 185 to lock the ring members in registration with one another.

The steps of a method of using the tissue retrieval system 100 can be understood from FIGS. 1-5 and 7A-7C. In general, the introducer sleeve 115 of FIG. 1 is introduced through an incision 162 in a body wall (e.g., abdominal wall) with the retrieval bag 125 carried in the distal section of passageway 118 in the introducer sleeve 115 (see FIG. 1). Thereafter, the retrieval bag 125 is deployed in the body cavity as the clinician pushes the deployment shaft 120 distally wherein the spring arms 148A, 148B open the rim portion 140 of the bag 125 (see FIG. 2). Next, the clinician used an instrument such as a grasper introduced through another port in the body wall to grasp a tissue specimen and insert it into the retrieval bag 125. Next, the clinician used a grasper to grasp the rim portion 140 of the bag 125 and withdraws the deployment shaft 120 and spring arms 148A, 148B from the introducer sleeve 115. It should be appreciated that the grasper can be introduced through any incision in the abdominal wall as there typically would be additional incisions for an endoscope and other tools. Next, afterthe clinician has the tissue specimen captured in the bag 125, the clinician grasps the rim portion 140 of bag 125 with a grasper 202 and pulls the rim portion 140 through the incision 162 Thereafter, the clinician couples the support ring assembly 180 to the bag 125 as illustrated in FIGS. 7A-7C. Finally, the clinician cuts the tissue specimen exposed in the incision 162 and periodically upwardly lifts the lifting bands 160A-160D to elevate the tissue specimen into the incision 162 where it can be cut into smaller dimensions to allow it to be withdrawn through the incision 162, without expanding the incision dimension (see FIG. 7C). As can be seen in FIG. 8B, the lifting bands 160A-160D within the incision 162 will reposition within the wider guide channels 170A-170D and overlap one another. Thus, there will be multiple layers of cut-resistant film material in the incision 162 to prevent a clinician's scalpel from cutting through the multiple layers of film comprising the entire wall 142 of the bag 125 in the incision.

Figure 10C:
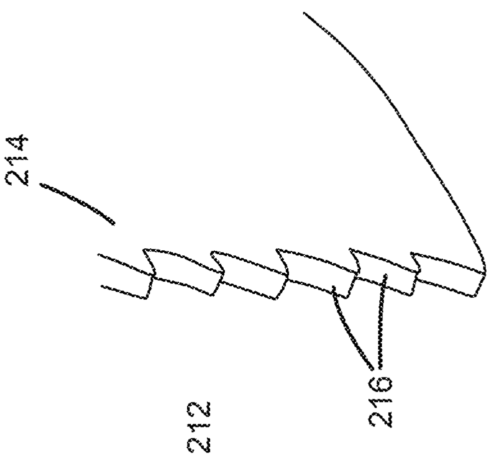
FIG. 10C shows an alternative lifting band with edge barbs to prevent back slippage.
Figure 10B:
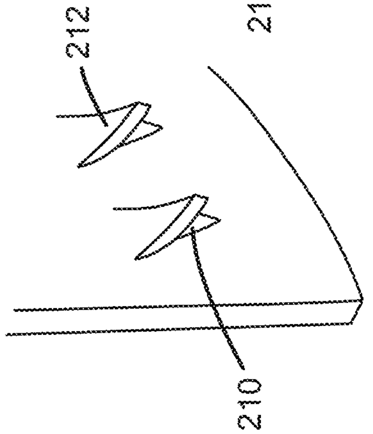
FIG. 10B shows an enlarged view of a portion of a lifting band with film barbs to prevent back slippage of the bands in a guide channel.
Figure 10A:
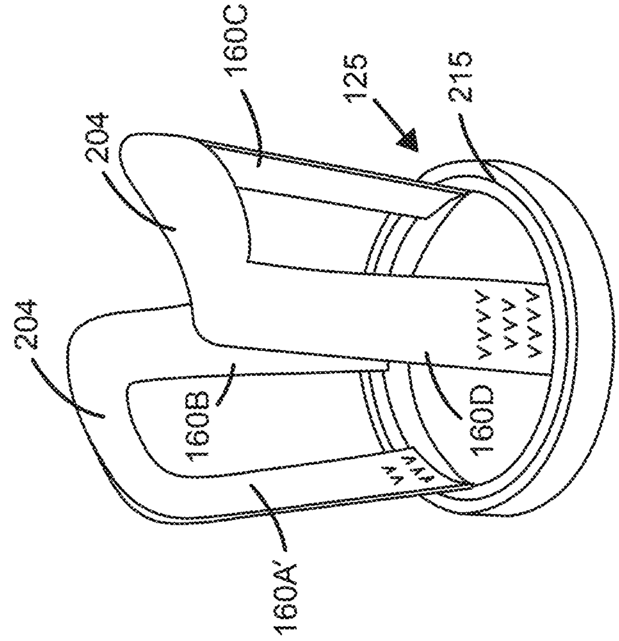
FIG. 10A illustrates another variation of a retrieval bag with a film handle between adjacent lifting bands.

A further advantage of the variation of retrieval bag 125 shown above is that clinician or assistant can lift all the lifting bands 160A-160D at the same time to thereby lift the tissue specimen in the same orientation to the incision 162. However, the clinician optionally can lift a single band or two bands to re-orient the tissue specimen T which will tend to roll and re-orient the part of the tissue specimen T exposed in the incision 162. This option of lifting, rolling, and/or re-orienting the tissue specimen T is not possible with other commercial retrieval bags that only lift all walls with a bag at the same time, typically by rolling up the upper edge of the bag. In a variation, FIG. 10A shows a bag 125 where adjacent lifting bands 160A' to 160D' are coupled with a proximal film handle portion 204 lift two bands with single hand of the clinician or assistant.

In general, since the tissue bands 160A-160D are compressed and constrained in the incision 162 after the bands are lifted as shown in FIGS. 7A-7C, the bands 160A-160D will not slip backwards to increase the depth of the bag. In a variation, a feature is provided to prevent back-slippage of the lifting bands 160A-160D. FIG. 10B illustrates a portion of a lifting band 160A that has cuts 210 therein to create film barbs 212 that can be pulled through the opening 188 of channels 170A-170B in the wall 142 of the bag 125 but will flip outwardly as barb elements to prevent back-slippage of the lifting bands. In another variation shown in FIG. 10C, the edges 214 of a lifting band 160A can have edge features or barbs 216 that catch on edges of the guide channel openings 188 to prevent back-slippage of the bands. Various other mechanisms can be used for preventing back-slippage of the lifting bands such as separate clips, etc. to lock the lifting bands in the superior edge 215 of the outer support ring 185 (see FIG. 10A).

Figure 11A:
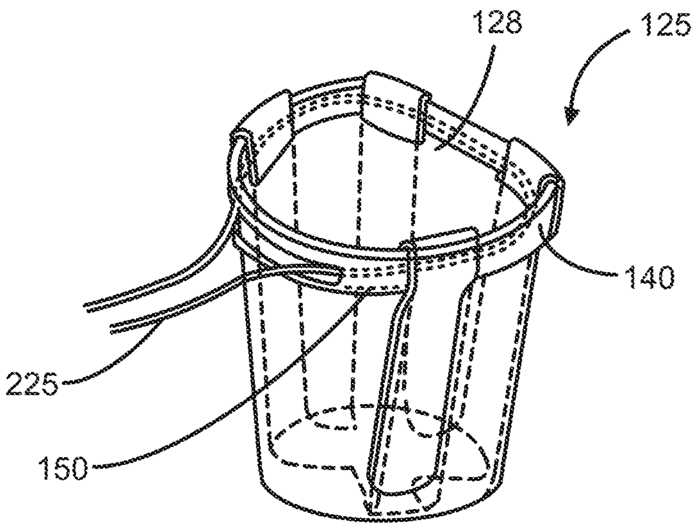
FIG. 11A shows another variation of a retrieval bag that includes a cinch cord.
Figure 11B:
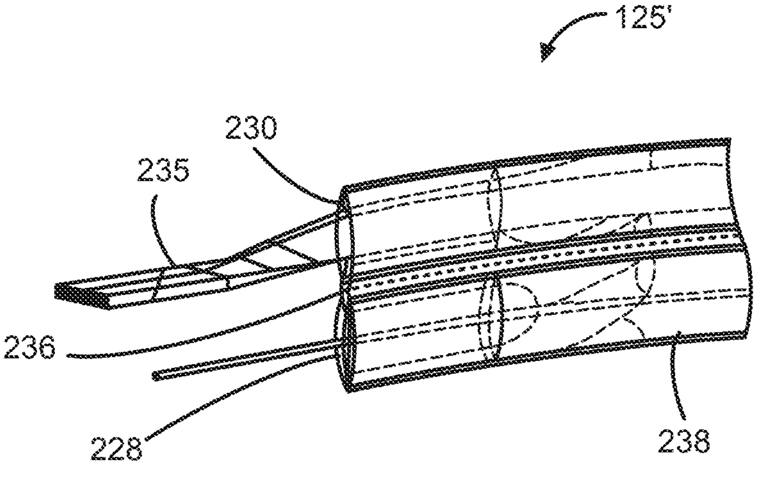
FIG. 11B illustrates a portion of a bag rim that has a spring support in a first channel in the bag rim and a cinch cord in a second channel in the bag rim with the tear-away joint in the film wall.

In another variation referring to FIG. 11A, a retrieval bag 125 of the type shown in FIGS. 3-5 and 7A can also carry a cinching mechanism for further control over the bag opening 128. In FIG. 11A, a cinch cord 225 is provided in channel 150 (or a separate cinch channel) in the rim portion 140 of the bag 125. The cinch cord 225 or closing cord is threaded through this channel 150, allowing the clinician to cinch the open end 128 of the bag 125 closed after the tissue specimen is captured in the bag. This cinching action helps secure the contents of the bag and prevents spillage during withdrawal of the rim portion 140 of the bag outwardly through an incision 162. In another variation shown in FIG. 11B, the retrieval bag 125' can have a cinch channel 228 adjacent to a support ring channel 230 that carries a support ring 235. The variation of FIG. 11B also is configured with a perforated 360° tear-away line 236 in the bag wall 238 wherein cinching the bag 125' will separate the bag from the support ring 235. In this variation, the support ring 235 does not need to be removable from the support ring channel 230 and can optionally extend in 360° around the bag rim.

Figure 12A:
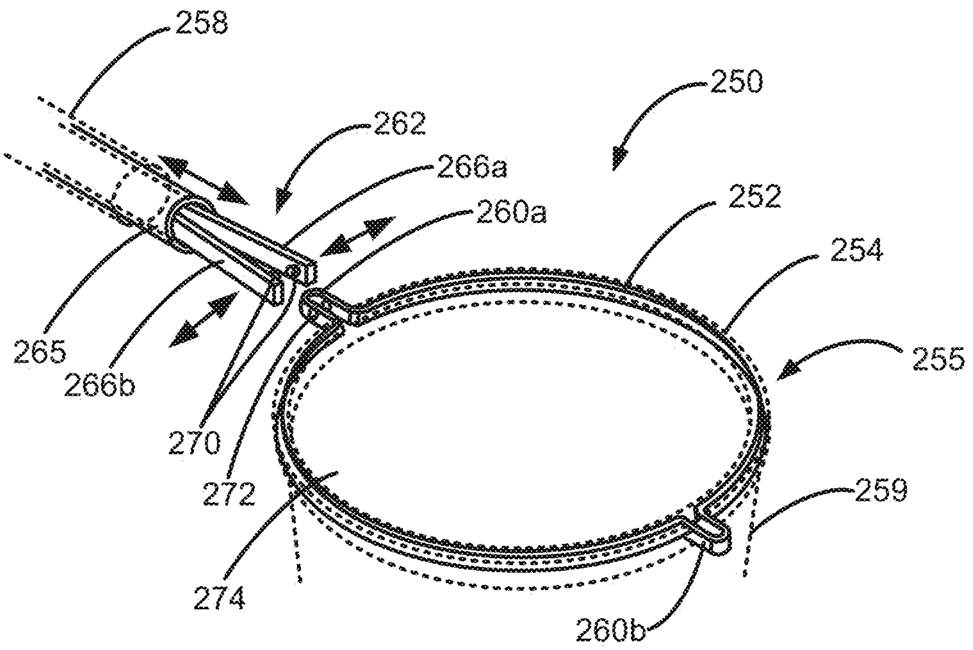
FIG. 12A illustrates another variation of a retrieval bag with a non-detachable and collapsible support ring carried in the bag rim.

Now, turning to FIG. 12A, another variation of tissue retrieval system 250, is illustrated that is similar to previous variations except that a support ring 252 is carried in the superior rim 254 of the retrieval bag 255 and is not removable from the bag rim 254. As can be seen in FIG. 12A, the support ring 252 extends in 360° around the bag rim 254 and comprises a spring material adapted for flattening or collapsing of the ring 252 that then allows for (i) retraction into the introducer sleeve 258 in the pre-deployed bag configuration and (ii) constraining the bag rim 254 and support ring 252 when withdrawn through an incision in a body wall of the patient after capturing the tissue specimen in the bag 255. The support ring 252 in FIG. 12A has proximal and distal pre-bent portions 260*a* and 260*b* that are configured to allow for flattening the support ring 252. The support ring 252 thus holds open the bag rim 254 and bag wall 259 and also retracts tissue away from the open end of the bag 255 to assist in capturing a tissue specimen.

The variation of tissue retrieval system 250 of FIG. 12A further illustrates that the bag 255 and support ring 252 are detachable from the deployment assembly 262. FIG. 12A illustrates an introducer sleeve 258 in which the deployment assembly 262 is extendable and retractable from the sleeve 258. The deployment assembly 262 comprises an axially-slidable actuator sleeve 265 that slides over first and second spring-clamp arms 266*a*, 266*b* to clamp onto, or release, the proximal pre-bent portion 260*a* of the support ring 252. In this variation, the distal ends of the first and second spring-clamp arms 266*a*, 266*b* have projecting elements 270 that are adapted to clamp into apertures 272 or indentations in the pre-bent portion 260*a* of the ring 262. The clamp arms 266*a*, 266*b* can be clamped tightly or less tightly to allow tilting of the bag rim 254and support ring 252 with the projecting elements 270 and apertures 272 forming a pivot point. As will be described below, the clinician can use a grasper or other instrument to tilt the open end 274 of the bag 255 and support ring 252 and lock it in the tilted position to provide an optimal orientation of the bag open end for capturing a tissue specimen.

Figure 12B:
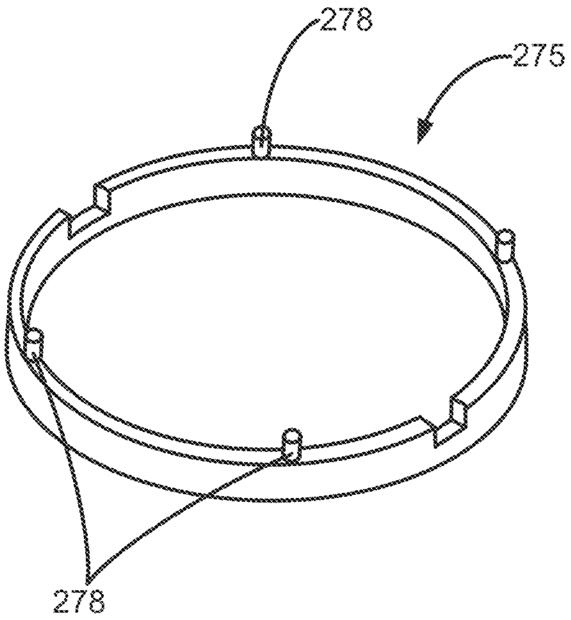
FIG. 12B illustrates a secondary support ring adapted for coupling to the bag rim of the retrieval bag of FIG. 12A.
Figure 12C:
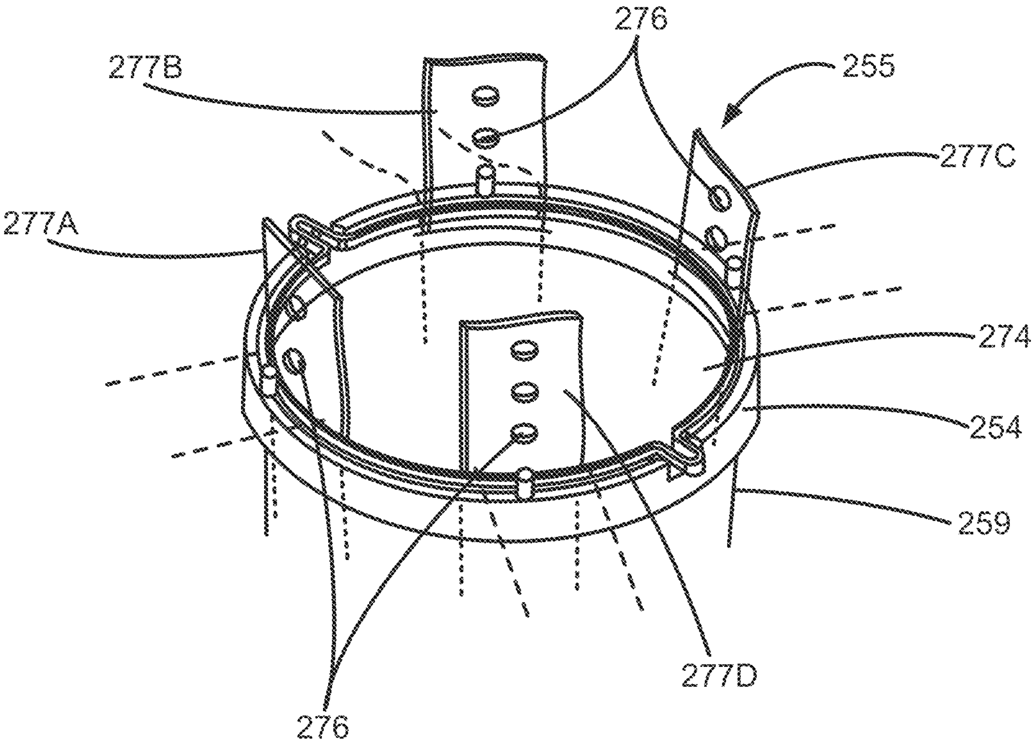
FIG. 12C illustrates the secondary support ring of FIG. 12B coupled to the retrieval bag of FIG. 12A.

FIGS. 12B and 12C illustrate an optional additional support component for use with the retrieval bag system 250 of FIG. 12A. As described above, it can be understood that retrieval bag 255 retains the support ring 252 and can be pulled through an incision as the ring 252 and bag rim 254 collapse. After the support ring 252 and bag rim 254 are outside the incision in the patient's body wall, the support ring 252 will hold open end the open end 274 of the bag 255. FIGS. 12B-12C illustrate a strengthening outer ring 275 which is used to counteract forces applied by the lifting bands when lifting a tissue specimen. The outer support ring 275 also has locking features for locking the lifting bands in a lifted position. In the variation shown in FIGS. 12A-12C, the locking features comprise apertures 276 in each of the lifting bands 277A-277D that can be hooked on projections or retaining posts 278 in the outer ring 275. In the variation of FIG. 12C, the lifting bands 277A-277D are also at least partly fabricated of a strong elastic material that can be stretched and tensioned in the bag wall 259. In such a variation, the support rings 252, 275 and bag rim 254 during use will pulled distally or downward against the patient's body and the elastic lifting bands 277A-277B then can be somewhat tensioned or highly tensioned to apply continuous lifting forces on the bottom of the bag 255 and the tissue specimen. In order to maintain the lifting bands 277A-277B in a tensioned position, the outer ring 275 thus provides the projections 278 for locking the lifted bands in a selected tensioned position.

As can be seen in FIG. 12C, each lifting band 277A-277B can be folded over (phantom view) to lock an aperture 276 onto a projecting post or projection 278. Thus, the retrieval system used elastic material capable of applying a continuous lifting force on bag during a procedure to lift the tissue specimen into the incision for cutting. Further, the bag 255 and support rings 252, 272 function as a self-retained retractor mechanism for retracting or opening the incision to facilitate cutting of the tissue specimen exposed in the incision. As can best be seen in FIG. 15E (a similar bag variation), the lifting forces on the lifting bands cause the bag rim and support rings to be pulled into contact with exterior of the patient's body as the bolus of the tissue specimen T in the retrieval bag is pulled into contact with the interior of the body wall. Thus, the tension on the bag wall 259 creates transverse retracting forces shown by arrows BB in FIG. 15E to retract the incision radially outwardly to the extent possible. In the variation of FIGS. 12-12C, the lifting bands 277A-277D can be elastomeric material only partly. For example, the superior or proximal portions of each lifting band outward of the bag rim 254 can a non-stretchable film material and the interior portions of the lifting bands extending to the bottom of the bag 255 can comprise an elastomeric material for providing continuous tensioning in the lifting of the bag wall 259.

Figure 13:
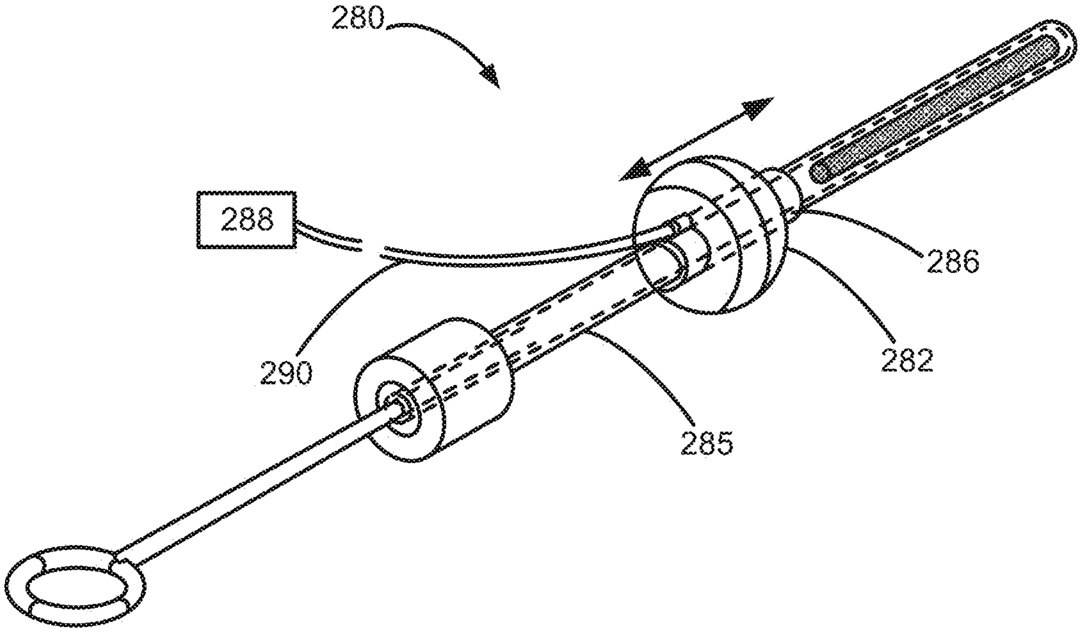

Now, turning to FIG. 13, another variation of retrieval system 280 is shown that is similar to that of FIGS. 1 and 2 with the addition of an occluder member 282 carried by the introducer sleeve 285. As can be seen in FIG. 13, the occluder member 282 is carried on a secondary sleeve 286, which is adapted for sliding back and forth over the introducer sleeve 285. The axial movement of the occluder member 282 over the introducer sleeve 285 is needed to allow the clinician to position the occluder member 282 in an optimal location in a body lumen, as can be understood from FIGS. 15A to 15D below. In another variation (not shown), the introducer sleeve 285 can carry a plurality of expandable balloons fixed to the introducer sleeve 285, and the clinician can inflate one or more selected balloons to optimally occlude the body lumen. In the variation shown in FIG. 13, the occluder member 282 comprises an inflatable balloon that is inflated from an inflation source 288 connected to an inflation tube 290 coupled to the occluder member 282. The inflation source 288 can deliver a fluid, such as a gas or a liquid, and can consist of a syringe, a pinch bulb, or any other suitable inflation mechanism.

Referring to FIG. 13, the occluder member 282 typically comprises an expandable component such as an inflatable balloon that is used to temporarily occlude or close off the lumen or pathway accessing a patient's body cavity. For example, the occluder member 282 can be used to occlude or close off the vaginal canal 292 in a trans-vaginal hysterectomy as shown in FIG. 15A. In this method, the retrieval system 280 is introduced trans-vaginally instead of through a laparoscopic access through an abdominal wall. As can be understood, the purpose of occluder member 282 is to prevent the inadvertent spillage of surgical fluids and to prevent escape of insufflation gases or fluids used to insufflate the patient's body cavity to provide a working space for the surgical procedure. The occluder member 282 alternatively can be fabricated of a block of biocompatible, resilient material that is both soft for patient comfort and sturdy enough to maintain its shape and pressure against the sidewalls of the lumen during the procedure.

FIGS. 14A-14B illustrate the working end 294 of the tissue retrieval system 280 of FIG. 13 that includes a mechanism for tilting the rim portion 2954 and opening 296 of bag wall 298 of retrieval bag 300 relative to the axis 302 of the introducer sleeve 285, which can assist in inserting a tissue specimen into the opening 296 of the bag 300. FIG. 14A illustrates a tilting mechanism that comprises a living hinge 305 in proximal portions of spring arms 310A and 310B that are otherwise similar to the spring arms 148A-148B shown in FIGS. 2 and 3. In other words, the deployment shaft 312 is advanced distally to deploy the bag 300 and the living hinge region 305 can be within or distally outward from the distal tip 314 of the introducer sleeve 285. Thus, the living hinge 305 can be advanced distally from introducer sleeve tip 314 to provide any desired angle or tilt of the rim portion 295 of the bag 300, wherein tilt can range from 0° to 90°.

FIGS. 15A-15D illustrate a method of using the tissue retrieval system 280 of FIGS. 13 and 14A-14B in a trans-vaginal hysterectomy. FIG. 15A illustrates the introducer sleeve 285 being introduced through the patient's vaginal canal 292 and through the vaginal colpotomy 316 (created by the surgical separation of the uterus 318 and cervix 320 from the pelvic floor complex) into the abdominal cavity 322. It can be seen that the occluder member 282 is in an expanded position to prevent the escape of insufflation gas from the abdominal cavity 322. FIG. 15B illustrates other instruments 324, 325, such as graspers, cutting devices, and an endoscope introduced through the abdominal wall 326 to mobilize the uterus 318.

FIG. 15B further shows that the clinician advances the deployment shaft distally and the spring arms 310A 310B extend outwardly to open the bag 300 as well as tilting the rim portion 295 and opening 296 of the bag 300 as the living hinge 305 extends distally from the distal tip 314 of the introducer sleeve 285. FIG. 15C shows a grasper and other tools 324, 325 being used to move the mobilized uterus 318 into the interior of the bag 300. FIG. 15D then shows that the introducer sleeve 285 and spring arms 310A, 310B after being retracted and withdrawn from the patient's vaginal canal 292. In FIG. 15D, another grasper 332 has been used to withdraw the rim portion 295 of bag 300 through the incision or colpotomy 316 to expose the tissue specimen in the incision outside the patient. FIG. 15D further shows that the ring assembly 180 as shown in FIGS. 7A-7C has been coupled to the rim portion 295 of the retrieval bag 300. Thus, in FIG. 15D, the tissue specimen is then prepared for cutting with tool 335 and extraction through the neck 336 of the retrieval bag 300 as described above.

Figure 15E:
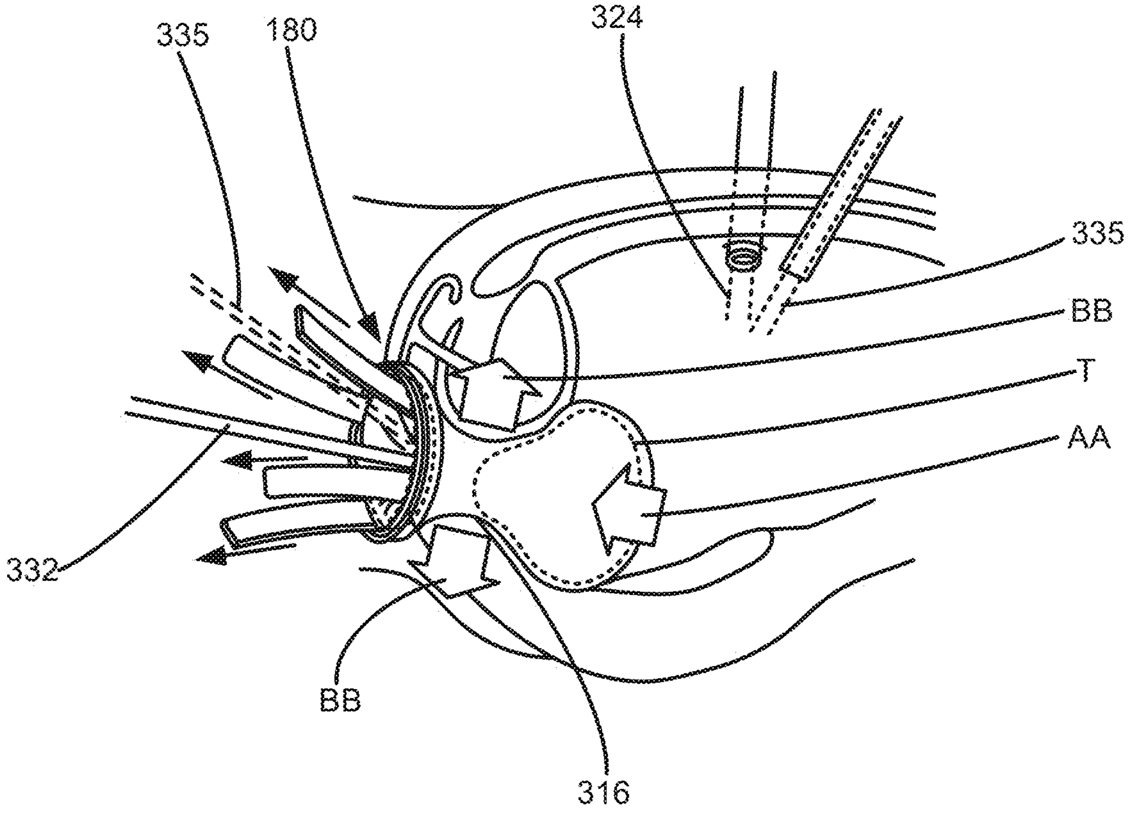

FIG. 15E illustrates a subsequent step wherein the lifting bands have been lifted, causing the bag rim and support rings to be pressed into contact with exterior of the patient's body as the tissue specimen T and retrieval bag are pulled in the direction of arrow AA into contact with the interior of the body wall. Thus, the shortening forces on the bag wall 298 create transverse retracting forces shown by arrows BB to retract the incision 316 radially outward to a more open position. This radial retraction of the colpotomy or incision 316 is advantageous as the wider opening exposes more surface area of the tissue specimen T for cutting and reduction in size.

FIG. 16 illustrates a working end of another variation of retrieval system 340 that includes a different mechanism to tilt rim portion of a retrieval bag. In this variation, the spring arms 345A-345B are fixed to a pivot pin 346 that rotates within a bore 348 in the extendable deployment member 350 to thereby allow the spring arms to move together to tilt the bag rim. In this variation, the pivot pin 346 has a tight fit in bore 348 or has ratcheting surfaces to generally maintain the bag rimin any selected tilted position, wherein any tilted position can be overcome by forces applied by the clinician with a grasper tilting the rim. In this variation, the clinician uses a grasper to engage and tilt bag rim in the abdominal cavity to any selected tilted angle. After capturing the tissue specimen in the bag, the clinician again uses the grasper to revert the tilt angle to an angle where the spring arms 345A-345B can be retracted into the introducer sleeve 355.

FIG. 17 illustrates another variation of tissue specimen retrieval system 360 that is similar to variation of FIG. 16 except that the handle 362 and introducer sleeve 365 carry an actuator rod 366 for assisting in mechanically tilting the rim 368 of the bag 370. FIG. 17 shows that the spring arms or 360° support ring 372 again has a pivot pin 375. Extension of the actuator rod 366 causes a spring 376 to tilt the support ring 372 upwardly. In another variation (not shown), the actuator rod 366 can mechanically tilt a lever arm to thereby tilt the support ring 372.

A person of ordinary skill in the art will recognize that any process or method disclosed herein can be modified in many ways. The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed.

The various exemplary methods described and/or illustrated herein may also omit one or more of the steps described or illustrated herein or comprise additional steps in addition to those disclosed. Further, a step of any method as disclosed herein can be combined with any one or more steps of any other method as disclosed herein.

The processes as described herein can be configured to perform one or more steps of any method disclosed herein. Alternatively or in combination, the processes can be configured to combine one or more steps of one or more methods as disclosed herein.

Unless otherwise noted, the terms "connected to" and "coupled to" (and their derivatives), as used in the specification and claims, are to be construed as permitting both direct and indirect (i.e., via other elements or components) connection. In addition, the terms "a" or "an," as used in the specification and claims, are to be construed as meaning "at least one of." Finally, for ease of use, the terms "including" and "having" (and their derivatives), as used in the specification and claims, are interchangeable with and shall have the same meaning as the word "comprising.

It will be understood that although the terms "first," "second," "third", etc. may be used herein to describe various layers, elements, components, regions or sections without referring to any particular order or sequence of events. These terms are merely used to distinguish one layer, element, component, region or section from another layer, element, component, region or section. A first layer, element, component, region or section as described herein could be referred to as a second layer, element, component, region or section without departing from the teachings of the present disclosure.

As used herein, the term "or" is used inclusively to refer items in the alternative and in combination.

As used herein, characters such as numerals refer to like elements.

Embodiments of the present disclosure have been shown and described as set forth herein and are provided by way of example only. One of ordinary skill in the art will recognize numerous adaptations, changes, variations and substitutions without departing from the scope of the present disclosure. Several alternatives and combinations of the embodiments disclosed herein may be utilized without departing from the scope of the present disclosure and the inventions disclosed herein. Therefore, the scope of the presently disclosed inventions shall be defined solely by the scope of the appended claims and the equivalents thereto.

What is claimed is:

1. A tissue retrieval system comprising:

a retrieval bag having an open end and a bag wall around an interior space extending to a closed end, the retrieval bag having a rim portion at the open end;

the retrieval bag adapted for an extended position wherein the closed end is extended a selected depth away from the rim portion and progressively collapsed positions wherein the closed end is lifted toward the open end; and a plurality of lifting members carried in the bag wall and configured to be withdrawn from the retrieval bag away from the rim for lifting the closed end toward the open end.

2. The tissue retrieval system of claim 1 wherein the bag wall is assembled from a polymeric thin film material.

3. The tissue retrieval system of claim 1 wherein the plurality of lifting members comprise at least one of a polymeric thin film material and a thread.

4. The tissue retrieval system of claim 1 wherein the plurality of lifting members are at least partly elastic.

5. The tissue retrieval system of claim 4 wherein the bag wall is configured with at least three guide channels each with a lifting member therein.

6. The tissue retrieval system of claim 5 wherein the at least three guide channels include at least two adjacent guide channels in the bag wall that at least partly overlap.

7. The tissue retrieval system of claim 1 wherein at least one of the plurality of lifting members has a width of 40 mm or less.

8. The tissue retrieval system of claim 1 wherein at least one of the plurality of lifting members has a width ranging from 0.5 mm to 40 mm.

9. The tissue retrieval system of claim 1 wherein the plurality of lifting members are carried in guide channels.

10. The tissue retrieval system of claim 1 wherein a width of a guide channel in the bag wall is greater than the width of a lifting member from the plurality of lifting members disposed therein.

11. The tissue retrieval system of claim 1 further comprising a support ring coupled to the rim portion of the retrieval bag around the open end of the retrieval bag.

12. The tissue retrieval system of claim 11 wherein the support ring is attachable and detachable from the rim portion.

13. The tissue retrieval system of claim 11 wherein the support ring is fixed in the rim portion.

14. The tissue retrieval system of claim 1 further comprising an introducer sleeve extending about a longitudinal axis to a distal tip;

wherein the retrieval bag is foldable for a pre-deployed configuration for carrying in an interior passageway of the introducer sleeve; and an elongate deployment member axially translatable in the interior passageway to extend to retrieval bag outward from the distal tip of the introducer sleeve.

15. The tissue retrieval system of claim 14 wherein the elongate deployment member is coupled to at least one spring element adapted to hold open the open end of the retrieval bag.

* * * * *